United States Patent
Shen et al.

(10) Patent No.: US 9,702,832 B2
(45) Date of Patent: Jul. 11, 2017

(54) CT IMAGING METHODS AND SYSTEMS

(71) Applicant: NUCTECH COMPANY LIMITED, Beijing (CN)

(72) Inventors: Le Shen, Beijing (CN); Yuxiang Xing, Beijing (CN); Li Zhang, Beijing (CN); Zhiqiang Chen, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 367 days.

(21) Appl. No.: 14/304,848

(22) Filed: Jun. 13, 2014

(65) Prior Publication Data

US 2014/0369458 A1 Dec. 18, 2014

(30) Foreign Application Priority Data

Jun. 14, 2013 (CN) .......................... 2013 1 0234787

(51) Int. Cl.
*A61B 6/03* (2006.01)
*G01N 23/04* (2006.01)
(Continued)

(52) U.S. Cl.
CPC ........... *G01N 23/046* (2013.01); *A61B 6/032* (2013.01); *A61B 6/4241* (2013.01); *A61B 6/482* (2013.01);
(Continued)

(58) Field of Classification Search
CPC ....... A61B 6/032; A61B 6/4241; A61B 6/482; A61B 6/5205; A61B 6/5258;
(Continued)

(56) References Cited

U.S. PATENT DOCUMENTS

2003/0169847 A1* 9/2003 Karellas ................. A61B 6/481
378/98.3
2011/0058719 A1 3/2011 Trzasko et al.
2011/0150183 A1 6/2011 Wu et al.

FOREIGN PATENT DOCUMENTS

CN 101040781 A 9/2007
CN 101900695 A 12/2010
(Continued)

OTHER PUBLICATIONS

Szczykutowicz et al.; "Dual energy CT using slow kVp switching acquisition and prior image constrained compressed sensing"; Physics in Medicine and Biology; 2010; vol. 55; p. 6411-6429.
(Continued)

*Primary Examiner* — Glen Kao
(74) *Attorney, Agent, or Firm* — Baker & Hostetler LLP

(57) ABSTRACT

Disclosed is a CT imaging method and system. The method includes: CT scanning an object with a dual-energy CT system to obtain a first complete set of projection data in a first scan mode, and to obtain a second incomplete set of projection data in a second scan mode; reconstructing a first attenuation coefficient image of the object from the first set of projection data, and extracting, from the first attenuation coefficient image, prior structure information of the object indicating edge intensity; and reconstructing a second attenuation coefficient image of the object from the second incomplete set of projection data using the extracted prior structure information as a constraint. With the method using the prior structure information of the imaged object as a constraint in reconstruction, it is possible to dramatically reduce an amount of data required for reconstruction, and achieve satisfactory effects even with ill-conditioned problems of limited-angle and inner reconstruction.

20 Claims, 9 Drawing Sheets

---

S141: CT SCAN AN OBJECT WITH A DUAL-ENERGY CT SYSTEM TO OBTAIN A FIRST COMPLETE SET OF PROJECTION DATA IN A FIRST SCAN MODE, AND TO OBTAIN A SECOND INCOMPLETE SET OF PROJECTION DATA IN A SECOND SCAN MODE

S142: RECONSTRUCT A FIRST ATTENUATION COEFFICIENT IMAGE OF THE OBJECT FROM THE FIRST SET OF PROJECTION DATA, AND EXTRACT, FROM THE FIRST ATTENUATION COEFFICIENT IMAGE, PRIOR STRUCTURE INFORMATION OF THE OBJECT INDICATING EDGE INTENSITY

S143: RECONSTRUCT A SECOND ATTENUATION COEFFICIENT IMAGE OF THE OBJECT FROM THE SECOND INCOMPLETE SET OF PROJECTION DATA USING THE EXTRACTED PRIOR STRUCTURE INFORMATION AS CONSTRAINT

(51) Int. Cl.
*A61B 6/00* (2006.01)
*G06T 11/00* (2006.01)

(52) U.S. Cl.
CPC .......... *A61B 6/5205* (2013.01); *A61B 6/5258* (2013.01); *G06T 11/005* (2013.01); *G06T 11/006* (2013.01); *A61B 6/4085* (2013.01); *G06T 2211/408* (2013.01); *G06T 2211/436* (2013.01)

(58) Field of Classification Search
CPC ... G01N 23/046; G06T 11/005; G06T 11/006; G06T 2211/408; G06T 2211/436
See application file for complete search history.

(56) References Cited

FOREIGN PATENT DOCUMENTS

| | | |
|---|---|---|
| CN | 101900696 A | 12/2010 |
| CN | 102435621 A | 5/2012 |
| CN | 103136773 A | 6/2013 |
| WO | WO 2011/161558 A1 | 12/2011 |

OTHER PUBLICATIONS

Chen et al.; "Temporal resolution improvement using PICCS in MDCT cardiac imaging"; Medical Physics; Jun. 2009; vol. 36 No. 6; p. 2130-2135.
Yu et al.; Compressed sensing based interior tomography; Physics in Medicine and Biology; 2009; vol. 54; p. 2791-2805.
European Patent Application No. 14172167.0; Extended European Search Report; dated Mar. 24, 2015; 10 pages.
Great Britain Patent Application No. 1410528.2; Combined Search and Examination Report; dated Dec. 11, 2014; 8 pages.
Wu et al.; "Multivariate Pursuit Image Reconstruction Using Prior Information Beyond Sparsity"; Signal Processing; © 2012; 11 pages.
Guo et al.; "EdgeCS: Edge Guided Compressive Sensing Reconstruction"; Jul. 2010; 10 pages.
Great Britain Application No. 1410528.2; Examination Report 18(3); dated Feb. 9, 2016; 4 pages.
Lian et al.; "Image reconstruction for CT based on compressed sensing and Art"; Optical Technique; vol. 35 No. 3; May 2009; p. 422-425 (contains English Abstract).
Chen et al.; "Temporal resolution improvement using PICCS in MDCT cardiac imaging"; Medial Physics; vol. 36 No. 6; Jun. 2009; p. 2130-2135.

* cited by examiner

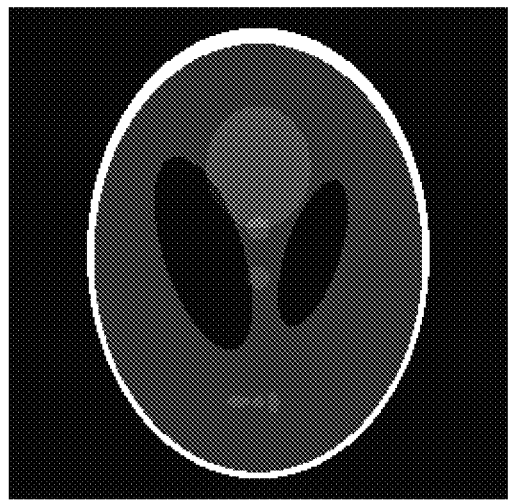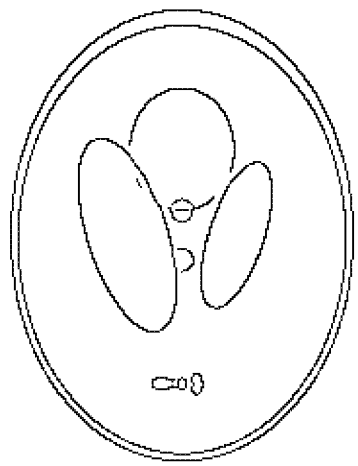
Fig. 1A　　　　Fig. 1B
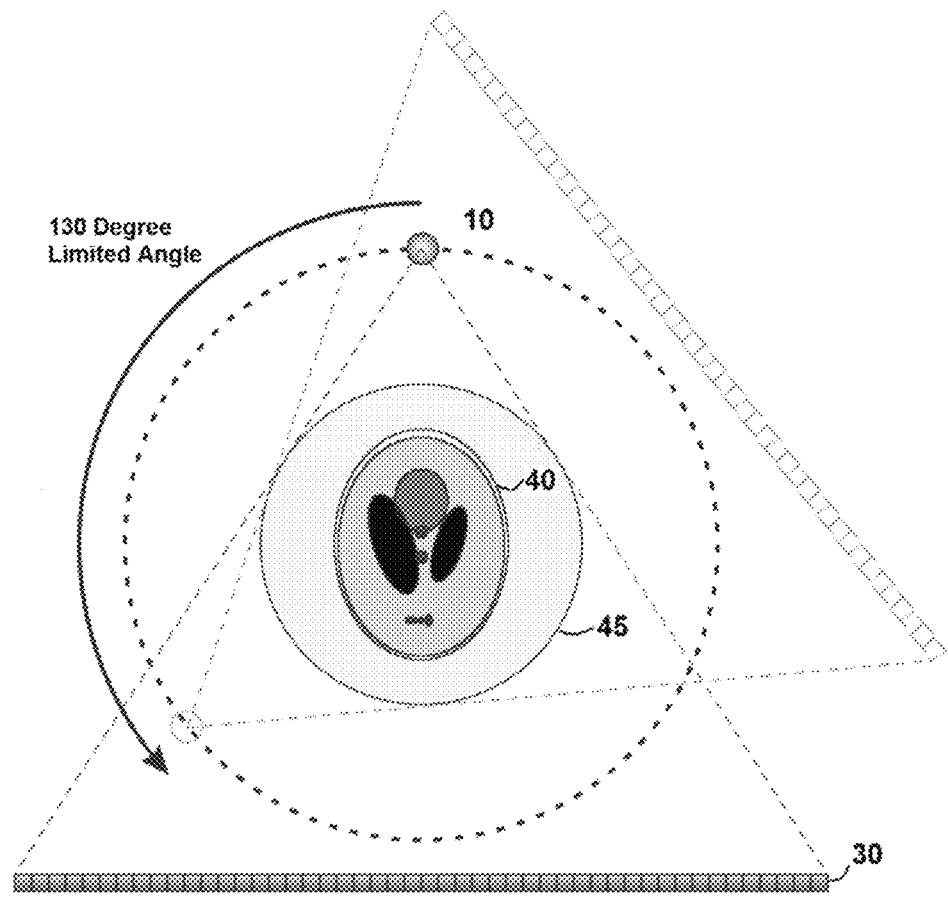
Fig. 2

CT IMAGING METHODS AND SYSTEMS

CROSS-REFERENCE TO RELATED APPLICATION

This application claims priority to the Chinese Patent Application No. 201310234787.3, filed on Jun. 14, 2013, entitled "CT imaging Method and System", which is incorporated herein by reference in its entirety.

TECHNICAL FIELD

Embodiments of the present disclosure relates to radiography, and particularly to CT imaging methods and systems using prior structure information.

BACKGROUND

X-ray CT imaging systems are widely applied in various fields including medical service, safety inspection, and industrial lossless detection. A serial of projection data are captured through ray sources and detectors along certain tracks, and then restored through an image reconstruction algorithm to obtain a spatial distribution of linear attenuation coefficients of some section of an object. Image reconstruction refers to a process of restoring original attenuation coefficients from line integral data of linear attenuation coefficients, which is an inversion problem. Currently, a conventional Filter Back Projection (FBP) algorithm is mostly used in real applications, and it is an analytic algorithm based on processing of continuous signals. Iterative reconstruction technology also attains rapid development with a speed-up in computer processing. Compared with the analytic algorithm, the iterative algorithm can be used in more diversified conditions, and achieve a satisfactory reconstruction result even with various non-standard scanning tacks, low dose, incomplete projection data, or limited angles.

Recently, one of hotspots in CT imaging research is an CT image reconstruction method based on compress sensing. In accordance with the compress sensing theory, if some conditions are met, and a measured signal presents sparseness under some transform, the possibility that an original signal can be reconstructed accurately with only a few measurements is very high. Assume that the original signal has n components, and there are m measurement data, how can the original signal x* be reconstructed? Prior information and a "good" measurement matrix are essential. Here, the prior information refers to sparseness of a transform $\Psi$. It is required that the number of non-zero components of the signal after the sparse transform is not larger than the number of times by which incoherent measurement is performed on the signal:

$$\|\Psi x^*\|_0 < m \quad (1)$$

The measurement matrix should be as random as possible. A Gaussian random matrix, for example, may be a measurement matrix which satisfies the randomness requirement.

The original signal may be obtained by solving a constrained zero-norm minimization problem. The sparsest solution in zero-norm can be obtained from a set of all feasible solutions satisfying data measurement conditions:

$$x^* = \operatorname{argmin}\{\|\Psi x^*\|_0 : Ax = b\} \quad (2)$$

However, the zero-norm optimization problem is difficult to solve, and thus 1-norm is generally used to approximate the above problem:

$$x^* = \operatorname{argmin}\{\|\Psi x^*\|_1 : Ax = b\} \quad (3)$$

Total Variation (TV) is often used as sparse transform in CT reconstruction, and refers to integration of gradient modulus of a signal. The fundamental TV-constrained reconstruction method is to obtaining a solution which minimizes the total variation from a set of all feasible solutions meeting fidelity of measurement data of CT projection data:

$$\min\|\nabla x\|_1 \quad (4)$$
$$\text{s.t. } Ax = b$$

The reconstruction method based on TV minimization constraint achieves excellent effects in sparse sampling, low dose and inner reconstruction problems. Except the sparseness as prior information, information of a prior image may also be used to enhance quality of the reconstructed image. For example, a reconstruction method based on prior image constrained compress sensing (PICCS) utilizes similarity between prior and target images for reconstruction. When a differential image $x_p - x$ between the prior image $x_p$ and the target image x has a sparseness, or is rendered sparse through some transform, the prior image can be used to enhance reconstruction effects. PICCS has been successfully applied in cardiac dynamic imaging, perfusion imaging, dual-energy CT, and C-arm CT. PICCS requires a high similarity between the prior and target image, especially numerical approximation to each other. As such, the differential image can has better sparseness. PICCS is not applicable any more when the prior and target images have a large numerical difference, such as MeV-keV dual-energy CT.

SUMMARY OF THE DISCLOSURE

CT imaging method and system based on prior structure information are provided in view of one or more problems with the conventional technology.

In an aspect of the present disclosure, a CT imaging method is provided, comprising: CT scanning an object with a dual-energy CT system to obtain a first complete set of projection data in a first scan mode, and to obtain a second incomplete set of projection data in a second scan mode; reconstructing a first attenuation coefficient image of the object from the first set of projection data, and extracting, from the first attenuation coefficient image, prior structure information of the object indicating edge intensity and reconstructing a second attenuation coefficient image of the object from the second incomplete set of projection data using the extracted prior structure information as a constraint.

In another aspect of the present disclosure, a CT imaging method is provided, comprising: extracting prior structure information of an object from a first image reflecting an internal structure of the object, wherein the prior structure information indicates edge intensity; CT scanning the object with a CT system to obtain a set of projection data; and reconstructing a second image of the object from the set of project data using the extracted prior structure information as a constraint.

In a further aspect of the present disclosure, a CT imaging system is provided, comprising: a ray source configured to generate dual-energy X rays; a detection & collection device configured to receive dual-energy X rays penetrating an object; a control device configured to control the ray source and the detection & collection device to CT scan the object to obtain a first complete set of projection data in a first scan mode, and to obtain a second incomplete set of projection data in a second scan mode; and a reconstruction device configured to reconstruct a first attenuation coefficient image of the object from the first set of projection data, extract, from the first attenuation coefficient image, prior structure information of the object indicating edge intensity, and reconstruct a second attenuation coefficient image of the object from the second incomplete set of projection data using the extracted prior structure information as a constraint.

In a yet further aspect of the present disclosure, a CT imaging system is provided, comprising: a ray source configured to generate dual-energy X rays; a detection & collection device configured to receive dual-energy X rays penetrating an object; a control device configured to control the ray source and the detection & collection device to CT scan the object to obtain a set of projection data; and a reconstruction device configured to extract prior structure information of the object from a first image reflecting an internal structure of the object, wherein the prior structure information indicates edge intensity, and reconstruct a second image of the object from the set of project data using the extracted prior structure information as a constraint.

With the above embodiments using the prior structure information of the imaged object as a constraint in reconstruction, it is possible to dramatically reduce an amount of data required for reconstruction. Further, the present disclosure can achieve satisfactory effects even with ill-conditioned problems of limited angle and inner reconstruction.

BRIEF DESCRIPTION OF THE DRAWINGS

The following figures illustrate implementations of the present invention. The figures and implementations provide some embodiments of the present invention in a non-limiting and non-exclusive manner, in which:

FIGS. 1A to 1B show examples of image and prior structure information, respectively, involved in method and system according to embodiments of the present disclosure;

FIG. 2 is a schematic diagram depicting limited-angle CT scan used in method and system according to embodiments of the present disclosure;

DETAILED DESCRIPTION

Figure 3:
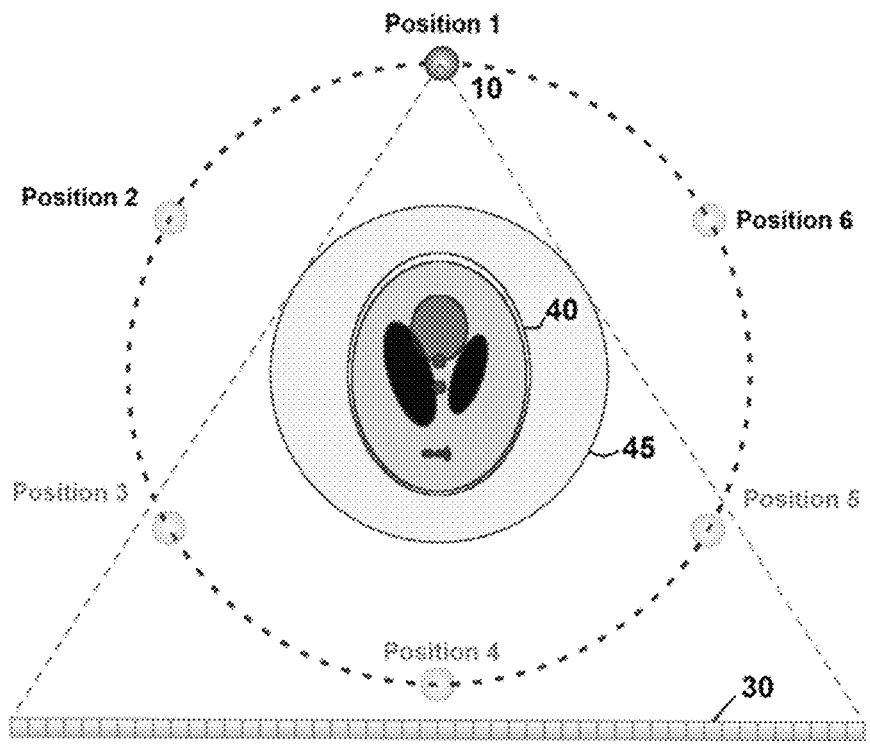
FIG. 3 is a schematic diagram depicting sparse-angle sampling CT scan used in method and system according to embodiments of the present disclosure.

In the following, particular embodiments of the present invention will be detailed. To be noted, the described embodiments are just intended for illustrating other than limiting the present invention. Numerous specific details are illustrated for a clear and thorough understanding of the present invention. It is apparent to those skilled in the art that these specific details are not necessary for implementation of the present invention. Detailed description of known circuits, materials or methods are omitted which otherwise may obscure the present invention.

Throughout the specification, reference to "an embodiment," "embodiments," an "example" or "examples" means that particular features, structures or characteristics described in connection with such embodiment or example are contained in at least one embodiment of the present invention. The phrase "an embodiment," "embodiments," "an example" or "examples" In various places throughout the specification does not necessarily refer to the same embodiment or example. Further, the particular features, structures or characteristics may be contained in one or more embodiments or examples in any appropriate combination and/or sub-combination. Those skilled in the art will appreciate that the term "and/or" herein indicates any or all combinations of one or more of the listed items.

In view of the problems with the conventional technology, embodiments of the present invention provide reconstructing an image of an object from complete or incomplete projection data by using prior structure information as constraint. For example, the prior structure information may be used to constrain the image during the CT reconstruction process, so that the reconstruction may be implemented with complete or incomplete data while guaranteeing image quality. In some embodiments, the structure information of an image may refer to information about boundaries and details having obvious grayscale difference in the image. The structure information are mostly used in image edge extraction and segmentation. FIG. 1B shows structure information extracted from the image of FIG. 1A, for example, using Laplace operator, Candy operator, discrete gradient transform, or adaptive thresholding, in some embodiments, the prior structure information may indicate a structure having a high similarity to that of a target image, no matter whether the prior image has a numerical dynamic range similar to that of the target image.

In some embodiments of the CT imaging method, an object is CT-scanned with a dual-energy CT system to obtain a first complete set of projection data in a first scan mode, and to obtain a second incomplete set of projection data in a second scan mode. A first attenuation coefficient image of the object is reconstructed from the first set of projection data, and prior structure information of the object is extracted from the first attenuation coefficient image. The prior structure information indicates edge intensity. Then, a second attenuation coefficient image of the object is reconstructed from the second incomplete set of projection data using the extracted prior structure information as a constraint, in these embodiments, the prior structure information may be obtained by using one of low-energy or high-energy images acquired in the dual-energy CT system, and then prior structure information may be used as constraint to reconstruct an image at the other one of the energy levels. In this way, a high-quality image can be reconstructed from incomplete projection data.

In some other embodiments of the CT imaging method, prior structure information of an object is extracted from a first image reflecting an internal structure of the object. The prior structure information indicates edge intensity. The object is CT-scanned with a CT system to obtain a set of projection data. Next, a second image of the object is reconstructed from the set of project data using the extracted prior structure information as a constraint. In these embodiments, the first image may be an image acquired from a previous CT imaging process of the object, or an image extracted from similar sectional images, or an artificially-generated image, such as a manually-made blueprint image (e.g., a Computer-Assisted-Design blueprint). The image for extracting the prior structure information may be any image that can reflect the internal structure of an object.

Solutions according to some embodiments are applicable in various fields such as lossless detection, medical diagnosis, and safety inspection. With some embodiments of the present disclosure that using structure information of the reconstructed object as prior information, it is possible to dramatically reduce an amount of projection data required for image reconstruction, without any requirement on the numerical dynamic range of the prior image. The methods of the present disclosure can be used to solve the image reconstruction quality problem due to incomplete data, such as the limited-angle CT scan problem in FIG. 2, the sparse-angle sampling CT scan problem in FIG. 3, the inner reconstruction CT scan problem in FIG. 4, and the detector undersampling CT scan problem in FIG. 5, and achieve satisfactory effects. Those skilled in the art will appreciate that embodiments of the present disclosure can be applied in various fields such as medical diagnosis, industrial lossless detection and safety inspection.

During reconstructing an image from incomplete projection data by using prior structure information as constraint, a method of iterative computation may be used, such as Algebra Reconstruction Technique (ART) method. If a target image is denoted as $f=\{f_1, f_2, \ldots, f_n\}$, projection data obtained by CT scan is denoted as $p=\{p_1, p_2, \ldots, p_m\}$, a line integral projection process is denoted as $$H\{h_{ij}\}_{m \times n},$$

and a noise variance of projection data is denoted as $\sigma^2=\{\sigma_1^2, \sigma_2^2, \ldots, \sigma_m^2\}$, the reconstruction problem through direct statistic iteration will become a weighted least square problem with a weight being an inverse of the noise variance of projection data:

$$\min\|Hf-p\|_W = \min(Hf-p)^T W(Hf-p) \tag{5}$$

"T" denotes transposition. A weighted matrix W reflects noise characteristic of projection data, and usually may take:

$$W = \mathrm{diag}^{-1}(\sigma^2) = \mathrm{diag}\left(\frac{1}{\sigma_1^2}, \frac{1}{\sigma_2^2}, \ldots, \frac{1}{\sigma_m^2}\right) \tag{6}$$

If the number of equations in the above equation system is less than the number of unknown variables, the equation system does not have a unique solution. In this case, it is necessary to add extra constraint in order to attain a unique solution. If TV minimization is used as constraint, an optimization problem will be derived as follows:

$$\min TV(f) = \min\|\nabla f\|_1 \text{ s.t. } \|Hf-p\|_W \leq \epsilon \tag{7}$$

Where the total variation may be approximated by calculating a sum of discrete gradient moduli of respective pixels in the image:

$$TV(f) = \|\nabla f\|_1 = \sum_{s,t}\sqrt{(f_{s,t}-f_{s,t-1})^2 + (f_{s,t}-f_{s-1,t})^2} \tag{8}$$

The method according to embodiments of the present disclosure introduces use of prior structure information as constraint. The structure information of an image here refers to information about boundaries and details having obvious grayscale difference in the image. Extracted structure information is mostly used in image edge extraction and segmentation, such as image edge extraction using an adaptive threshold.

Let the prior structure information of an image be $g=\{g_1, g_2, \ldots, g_n\}$, a weighted matrix is generated from the prior structure information as $G=\mathrm{diag}(g)=\mathrm{diag}\{g_1, g_2, \ldots, g_n\}$. The magnitude of the weight reflects the intensity of the edge. A larger weight represents a flatter region, and thus the TV smoothing is stronger; a smaller weight represents that the region is edge, and should not be smoothed by TV. As such, the optimization problem may be in the following form:

$$\min\|G\nabla f\|_1 + \lambda\|\nabla f\|_1 = \min\|(G+\lambda I)\nabla f\|_1 \tag{9}$$

$$\text{s.t. } \|Hf-p\|_W \leq \varepsilon$$

Here, $\epsilon$ is a quantity related to an overall level of noise in projection data, and $\lambda$ is to balance the prior structure information constraint and the TV constraint. The prior structure information is the dominant constraint when $\lambda \leq 1$, while the TV minimization is the dominant constraint when $\lambda > 1$. The weighted matrix W reflects noise characteristic of projection data, and I is identity matrix.

In an embodiment, the problem of equation (9) may be solved mainly in the following steps.

1) Extract prior structure information. The prior structure information may be obtained from a prior image through edge extraction, and then subjected to necessary preprocessing (e.g., smoothing, denoising, removing isolated points). Then, G is calculated.

2) Estimate a noise variance from projection data, calculate W and ϵ (W may be an identity matrix if it is impossible to estimate the noise), and select a weight λ for TV constraint.

3) Set an initial value for iteration as $f^0$.

4) Perform fidelity item update, for example, one round of update using ART iterative reconstruction algorithm:

$$f_{fit}^{f+1} = f_{fit}^k + w_{ij} \frac{p_j - H_j f_{fit}^k}{\|H_j\|^2} H_j^T \quad j = 1, 2, \ldots, m \quad (10)$$

In other embodiments, Simultaneous Algebra reconstruction Technique (SART) may be used for one round of update.

5) Perform an update with nonnegative constraint to set all points having a value less than zero in the result of ART iteration into zero:

$$f_{pos}^{k+1} = \max(0, f^{k+1}). \quad (11)$$

6) Perform an update with prior structure information constraint to reduce the value of weighted TV of the image:

$$f_{cons}^{k+1} = f_{cons}^{k+1} + \alpha \Box \nabla \left( \|(G + \lambda I) \nabla f_{pos}^{k+1}\|_1 \right) \quad (12)$$

Where "α" represents a step size of the most rapid decrease in the weighted TV.

7) Let $$f_{fit}^{k+1} = f_{cons}^{k+1},$$

and perform steps 4)~6) again; and repeat the iteration until a convergence condition (e.g., $$\|f_{fit}^* - f_{cons}^*\| \leq \varepsilon_{stop},$$

where $\varepsilon_{stop}$ represents a threshold for stopping iteration) is met.

In step 4), $H_j$ represents the jth line of the matrix H, and $w_{jj}$ represents the jth diagonal element of the matrix W. In addition to edge extraction, the prior structure information may be obtained in any other way, such as from a Computer-Assisted-Design blueprint.

Figure 6:
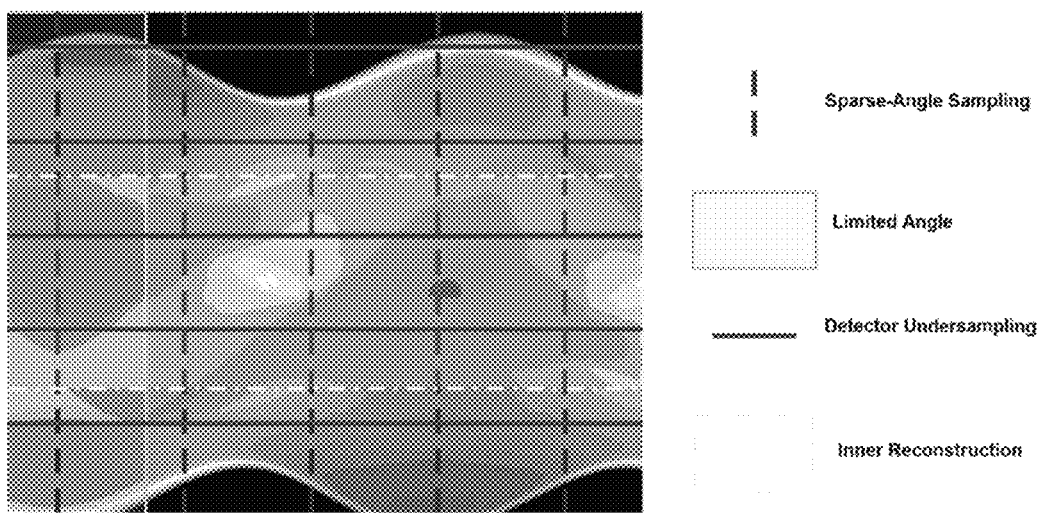
FIG. 6 is a schematic diagram depicting incomplete projection data involved in method and system according to embodiments of the present disclosure.
Figure 7:
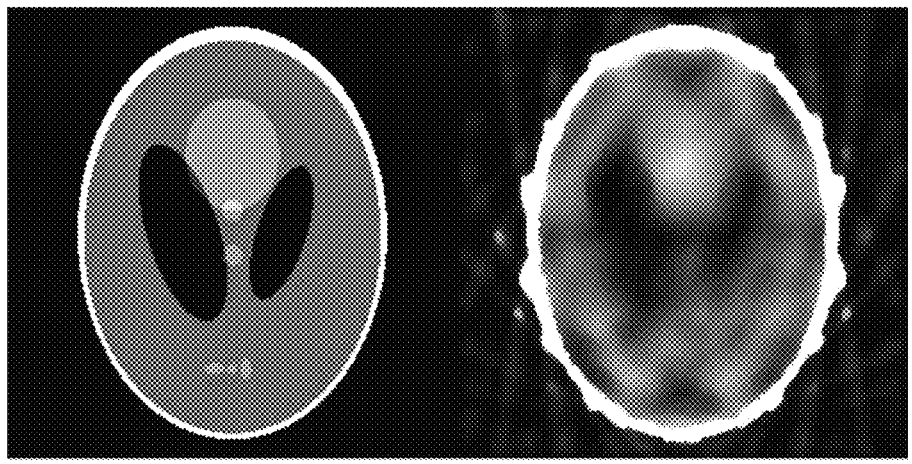
FIG. 7 shows a simulation result of method and system according to embodiments of the present disclosure in the condition of sparse-angle sampling CT scan.
Figure 8:
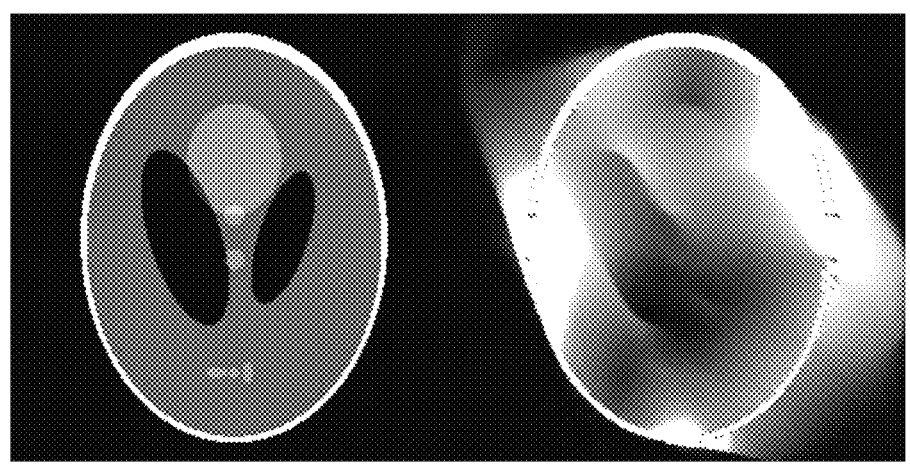
FIG. 8 shows a simulation result of method and system according to embodiments of the present disclosure in the condition of limited-angle CT scan.
Figure 9:
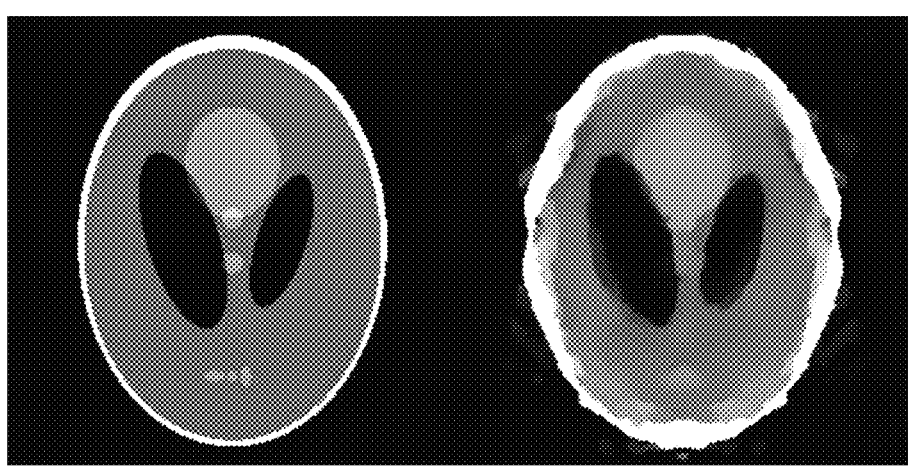
FIG. 9 shows a simulation result of method and system according to embodiments of the present disclosure in the condition of detector undersampling CT scan.

With the above method embodiments of the present disclosure using the prior structure information of the imaged object as a constraint in reconstruction, it is possible to dramatically reduce an amount of data required for reconstruction. Further, the present disclosure can achieve satisfactory effects even with ill-conditioned problems of limited angle and inner reconstruction. The embodiments of the present disclosure can provide a decrease in the number of detectors, and thus a cost reduction in manufacturing CT systems. The embodiments of the present disclosure allow narrowing angle coverage to reduce a layer thickness along z axis and improve time resolution, and performing local imaging to reduce radiation dose, and thus have a high practicability and a broad range of applications. FIGS. 2 to 5 illustrate four CT scan modes to which the method of the present disclosure can be applied. FIG. 6 shows actual sampling positions in a projection domain for the data obtained in these scan modes. FIG. 7 shows a reconstruction result of simulation with the method of the present disclosure in the case of angular sparse sampling mode, and FIG. 8 shows a reconstruction result of simulation with the method of the present disclosure in the case of limited-angle scan mode. FIG. 9 shows a result of simulation with the method and system of the present disclosure in the Me of detector undersampling CT scan mode.

FIG. 2 is a schematic diagram depicting limited-angle CT scan used in method and system according to embodiments of the present disclosure.

As shown in FIG. 2, X rays emitted from a ray source 10 penetrate an object 40 in a view field 45, and is received by a detector 30. The received X rays are converted into an electric signal, and further into a digital signal indicative of attenuation value. The digital signal is used as projection data for reconstruction in a computer. If prior structure information of the object is known, a high-quality image can be reconstructed even when the object 40 is CT-scanned at a limited angle (e.g., 130 degrees).

FIG. 3 is a schematic diagram depicting sparse-angle sampling CT scan used in method and system according to embodiments of the present disclosure.

As shown in FIG. 3, X rays emitted from a ray source 10 penetrate an object 40 in a view field 45, and is received by a detector 30. The received X rays are converted into an electric signal, and further into a digital signal indicative of attenuation value. The digital signal is used as projection data for reconstruction in a computer. If prior structure information of the object is known, a high-quality image can be reconstructed even when the object 40 is CT-scanned at multiple rotation positions (e.g., 130 degrees). In this way, a high-quality image can be reconstructed from incomplete projection data even if the object is under sparse-angle CT scan.

Figure 4:
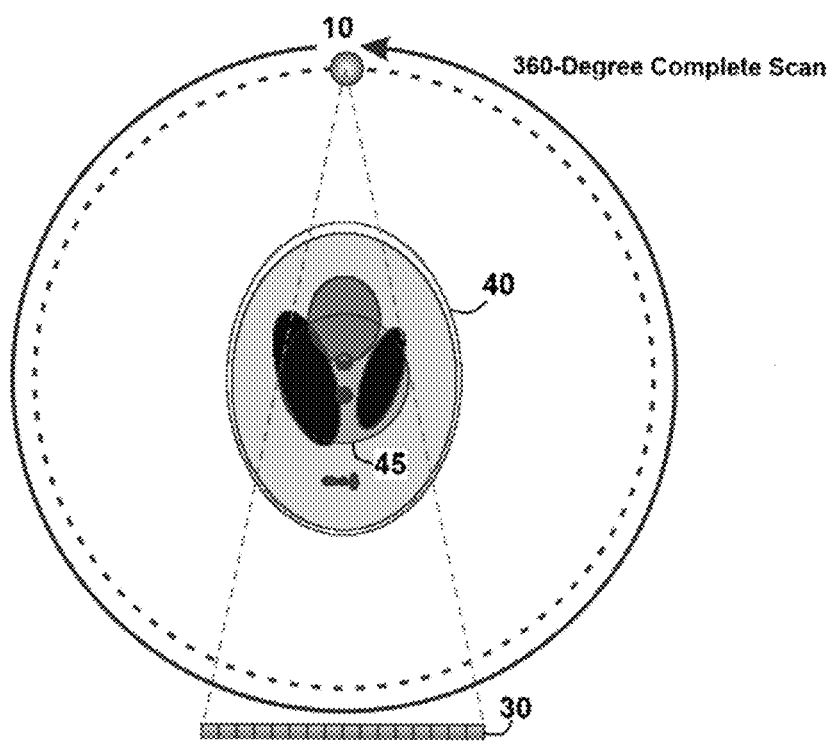
FIG. 4 is a schematic diagram depicting inner reconstruction CT scan used in method and system according to embodiments of the present disclosure.

FIG. 4 is a schematic diagram depicting inner reconstruction CT scan used in method and system according to embodiments of the present disclosure.

As shown in FIG. 4, X rays emitted from a ray source 10 penetrate an object 40 in a view field 45, and is received by a detector 30. The received X rays are converted into an electric signal, and further into a digital signal indicative of attenuation value. The digital signal is used as projection data for reconstruction in a computer. If prior structure information of the object is known, a high-quality image can be reconstructed even when the object 40 is CT-scanned in an inner reconstruction mode.

Figure 5:
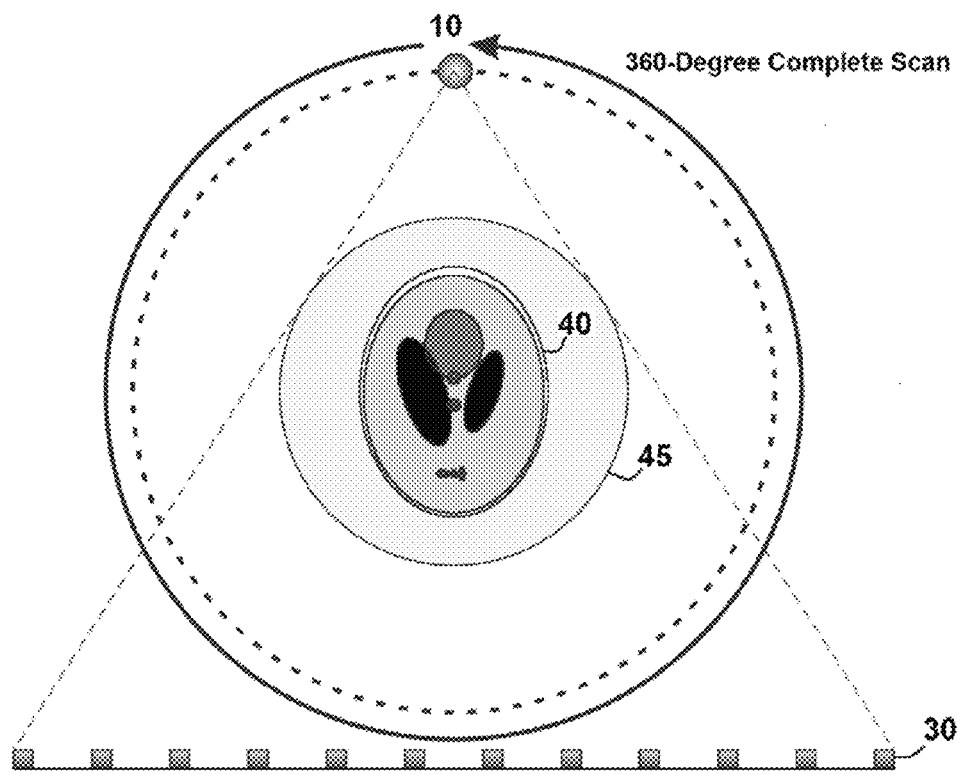
FIG. 5 is a schematic diagram depicting detector undersampling CT scan used in method and system according to embodiments of the present disclosure.

FIG. 5 is a schematic diagram depicting detector undersampling CT scan used in method and system according to embodiments of the present disclosure.

As shown in FIG. 5, X rays emitted from a ray source 10 penetrate an object 40 in a view field 45, and is received by a detector 30. The received X rays are converted into an electric signal, and further into a digital signal indicative of attenuation value. The digital signal is used as projection data for reconstruction in a computer. In this example, the detector 30 is arranged for undersampling, for example, by separating respective detector units from each other by a predefined distance. If prior structure information of the object is known, a high-quality image can be reconstructed even when the object 40 is CT-scanned in the undersampling state of the detector.

FIG. 6 is a schematic diagram depicting incomplete projection data involved in method and system according to embodiments of the present disclosure. As shown in FIG. 6, all the projection data obtained from the sparse-angle sampling CT scan, the limited-angle CT scan, the detector undersampling CT scan and the inner reconstruction CT scan are incomplete. With knowledge of prior structure information, a high-quality image can be reconstructed even from such incomplete projection data.

The right-side diagram in FIG. 7 shows a simulation result obtained by using the method of the present disclosure in the sparse-angle sampling CT scan, and the left-side diagram shows a simulation result obtained by using a conventional reconstruction method. The right-side diagram in FIG. 8 shows a simulation result obtained by using the method of the present disclosure in the limited-angle CT scan, and the left-side diagram shows a simulation result obtained by using the conventional reconstruction method. The right-side diagram in FIG. 9 shows a simulation result obtained by using the method of the present disclosure in the detector undersampling CT scan, and the left-side diagram shows a simulation result obtained by using the conventional reconstruction method.

Figure 10:
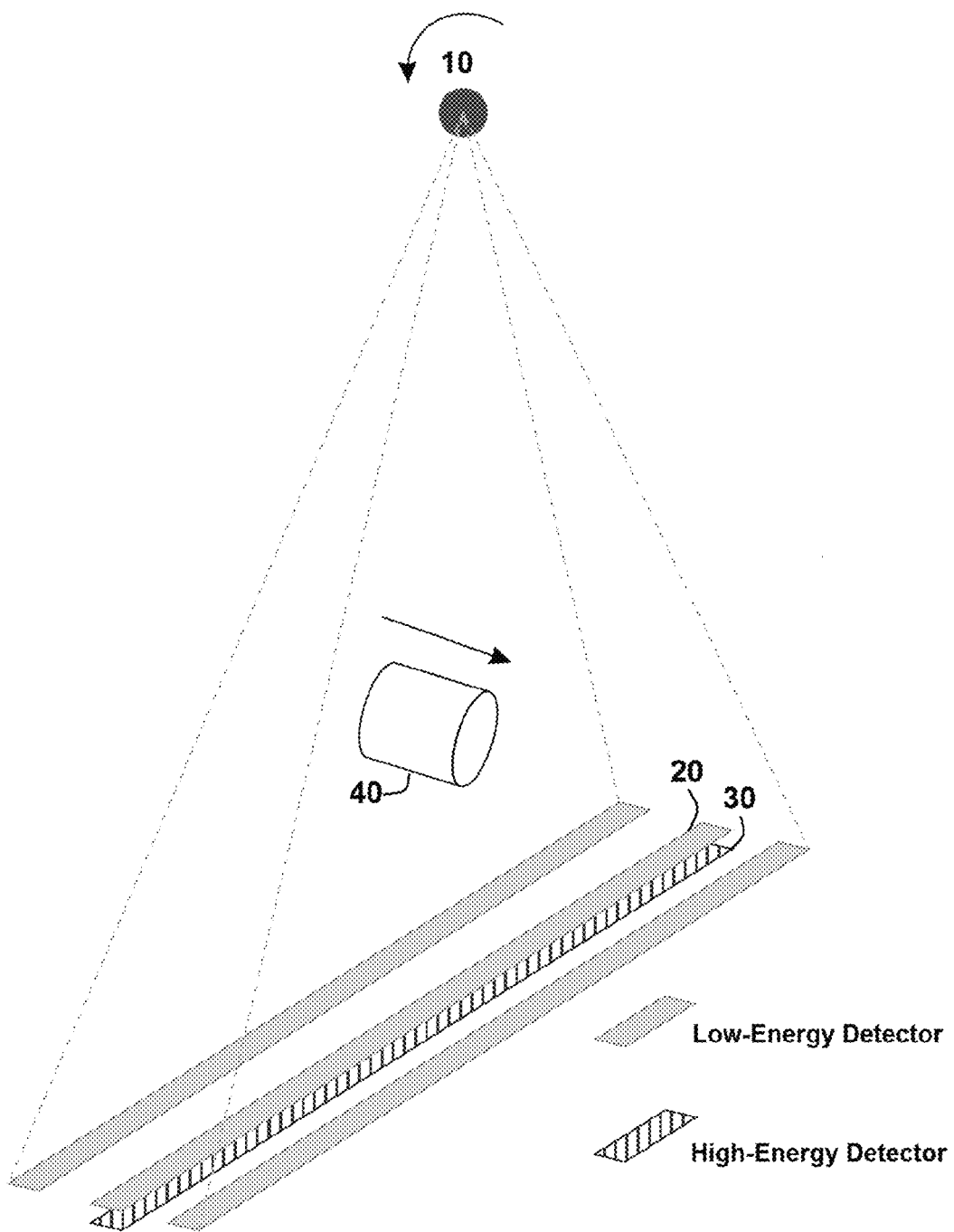
FIG. 10 is a schematic diagram depicting a dual-energy CT detector in the condition of limited-angle scan according to an embodiment of the present disclosure.

FIG. 10 is a schematic diagram depicting a dual-energy CT detector in the condition of limited-angle scan according to an embodiment of the present disclosure.

The dual-energy CT system includes multiple rows of low-energy detectors 20, and high-energy detectors 30 disposed behind part of the rows of low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection date may be obtained in a second scan mode. In particular, a limited-angle CT scan may be performed on the object with rays at a second energy level different from the first energy level, to obtain the second incomplete set of projection data. In the low-cost, dual-energy helical CT system as shown in FIG. 10, there are multiple rows of detectors including less rows of high-energy detectors than low-energy detectors, in order to reduce system cost. For example, there are 3 rows of low-energy detectors, and 1 row of high-energy detectors. When the low-energy detectors collect complete data, the high-energy detectors collect only ⅓ of the complete data, that is, covering only a limited-angle range of 120 degrees. The resulting low-energy attenuation coefficient reconstructed from the low-energy complete data may be used as a prior image from which structure information may be extracted. With the method according to embodiments of the present disclosure, the structure information may be used to constrain a limited-angle reconstruction problem at a high energy level, and then obtain a reconstruction result of high-energy attenuation coefficient. The photoelectric effect integral and Compton effect integral obtained from decomposition of duel-energy data are also incomplete, limited-angle data. The method described in the present disclosure can be used to reconstruct the photoelectric coefficient and Compton coefficient, and further obtain information about atomic number and electron density of material.

In the CT imaging system according to some embodiments, the ray source 10 generates dual-energy X rays. The detection & collection devices 20 and 30 receive dual-energy X rays that penetrate the object. The control device controls the ray source and the detection & collection devices to CT scan the object to obtain a first complete set of projection data in a first scan mode, and to obtain a second incomplete set of projection data in a second scan mode. The reconstruction device configured to reconstruct a first attenuation coefficient image of the object from the first set of projection data, extract, from the first attenuation coefficient image, prior structure information of the object indicating edge intensity, and reconstruct a second attenuation coefficient image of the object from the second incomplete set of projection data using the extracted prior structure information as a constraint.

Figure 11:
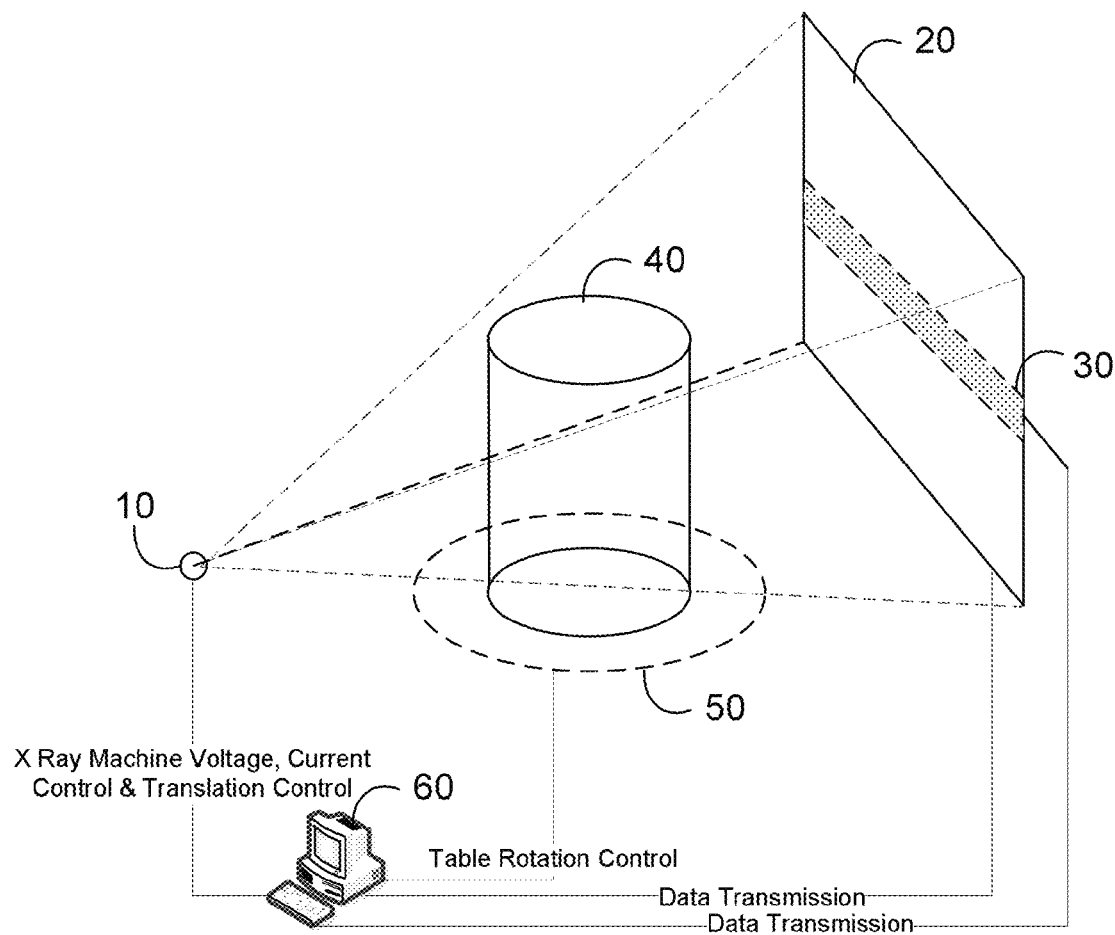
FIG. 11 is a schematic block diagram of a CT system according to embodiments of the present disclosure.

FIG. 11 is a schematic block diagram depicting an CT device according to embodiments of the present disclosure. The CT device includes an X ray source 10, a mechanic movement device & controller, and a detector & data collection system.

The X ray source 10 may be, for example, a X ray machine. A suitable focal spot size may be selected for the X ray machine depending on a resolution for imaging. The mechanic movement device & controller may include a table 50, a rack for the X ray machine and the detector, and a control system. The table 50 may be translatable to adjust a position of a rotation center, and the rack may be translatable so that the X ray machine and the detectors 20, 30 are aligned with the rotation center. The embodiment is described where the table is rotated, while the circular scan track or helical track of the rack is fixed. The table and the rack move relative to each other, and the present embodiment may also be implemented in the case that the table is static while the rack is rotated.

The detector & data collection system 20 and 30 may include low-energy X-ray detectors 20, and high-energy detectors 30 arranged behind part of the low-energy detectors. The data collection components may include a readout circuit, a collection trigger circuit, data transfer circuit, and the like.

The control and reconstruction apparatus 60 may include a controller and a reconstruction device. The controller is configured to control the operations of the CT system including mechanic rotation, electrical control, safety interlock control, and the like. The reconstruction device is configured for image reconstruction from projection data.

Although the above embodiments illustrate the dual-energy situation, the present disclosure is not limited thereto, and dual-energy may be not applied with knowledge of prior structure information. In the CT imaging system of the embodiment, the ray source generates X rays. The detector & collection device receives dual-energy X rays penetrating an object. The control device controls the ray source and the detection & collection device to CT scan the object to obtain a set of projection data. The reconstruction device extracts prior structure information of the object from a first image reflecting an internal structure of the object, wherein the prior structure information indicates edge intensity, and reconstructs a second image of the object from the set of project data using the extracted prior structure information as a constraint.

Figure 12:
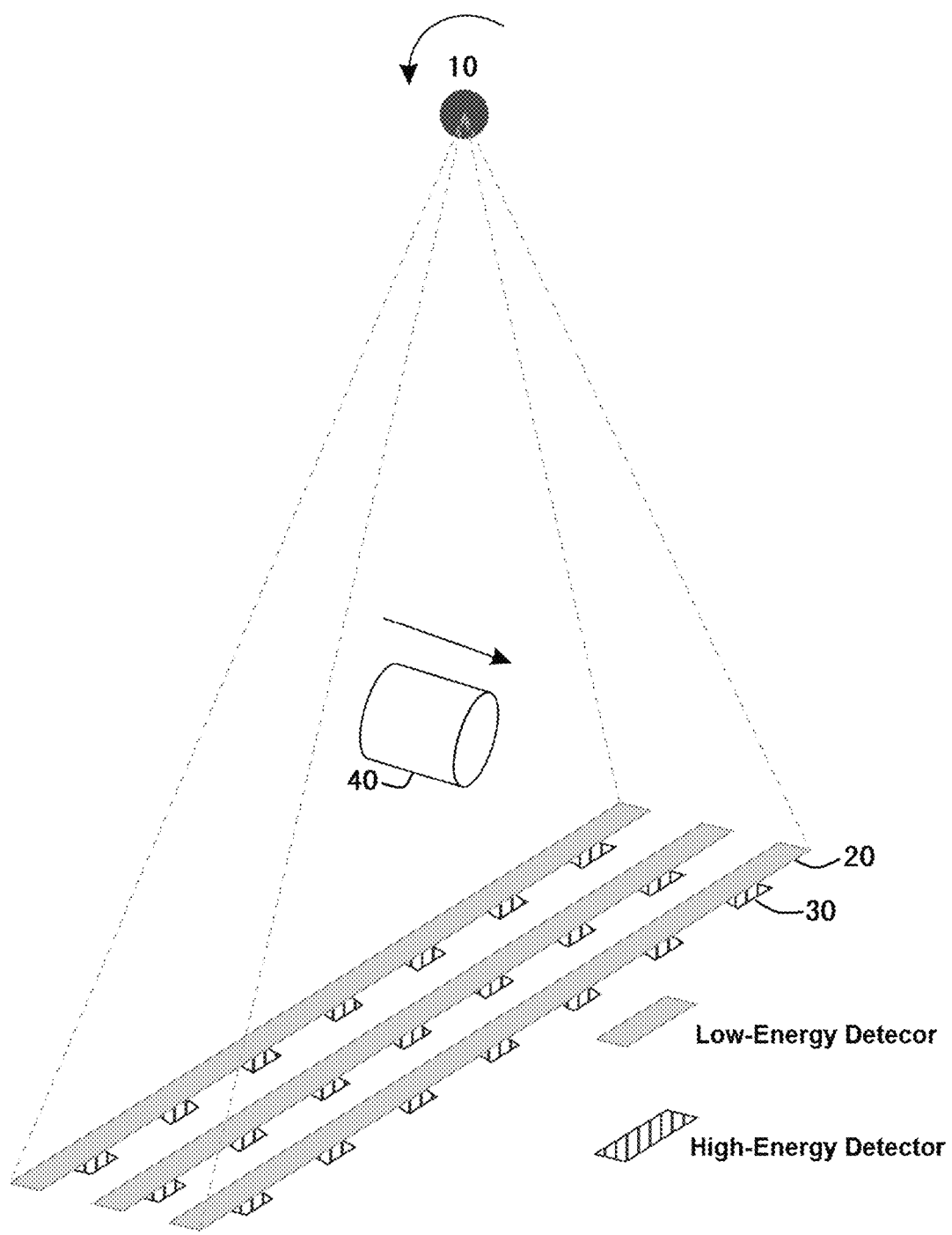
FIG. 12 is a schematic diagram depicting a dual-energy CT detector in the condition of detector undersampling according to another embodiment of the present disclosure.

FIG. 12 shows implementation of another low-cost dual-energy CT system. The dual-energy CT system may include at least one row of low-energy detectors, and a plurality of high-energy detectors which are uniformly provided behind part of the low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, a detector undersampling CT scan may be performed on the object with rays at a second energy level different from the first energy level, to obtain the second incomplete set of projection data. There may be a single or multiple rows of detectors in the system. The scan may be performed along a circular or helical track in the system. The number of the low-energy detector units may meet the requirement for collecting complete low-energy data. The number of the high-energy detector units may be reduced, so that, for example, one high-energy detector unit is provided per 10 low-energy detector units. As such, the number of the high-energy detector units is merely 10% of the low-energy detector units, thereby reducing system cost. With such arrangement of detectors, the low-energy data is complete, and may be used to reconstruct a high-quality image of low-energy attenuation coefficient, from which structure information may be extracted. The high-energy data is undersampled, and the method of the present disclosure may be used to solve the reconstruction problem in the detector undersampling condition, in order to obtain a reconstruction result of high-energy attenuation coefficient. The photoelectric effect integral and Compton effect integral obtained from decomposition of dual-energy data are also incomplete data of the same type as the high-energy data. The method described in the present disclosure can be used to reconstruct the photoelectric coefficient and Compton coefficient, and further obtain information about atomic number and electron density of material.

Figure 13:
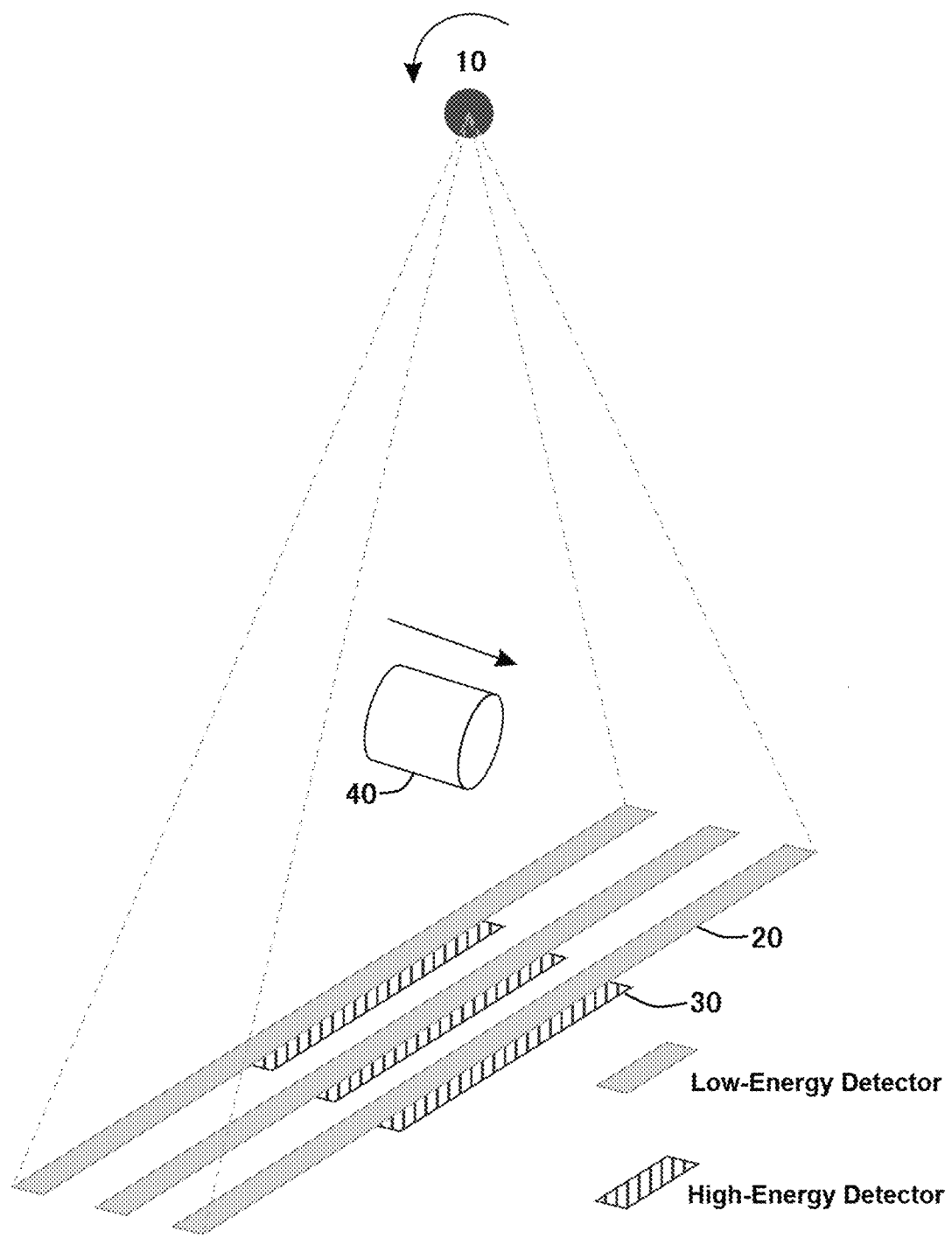
FIG. 13 is a schematic diagram depicting a dual-energy CT detector in the condition of inner reconstruction according to a further embodiment of the present disclosure.

FIG. 13 shows implementation of a further low-cost dual-energy CT system. The dual-energy CT system may include at least one row of low-energy detectors, and a plurality of high-energy detectors which are concentrated and provided behind part of the low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, an inner reconstruction CT scan may be performed on the object with rays at a second energy level different from the first energy level, to obtain the second incomplete set of projection data. There may be a single or multiple rows of detectors in the system. The scan may be performed along a circular or helical track in the system. The number of the low-energy detector units may meet the requirement for collecting complete low-energy data. The number of the high-energy detector units may be reduced, for example, by removing part of the detector units arranged near or at both of the edges, and keeping part of the detector units near or at the center. In an example, the high-energy detector units are provided behind only 25% of the low-energy detector units that are near the center. As such, the number of the high-energy detector units is merely 25% of the low-energy detector units, thereby reducing system cost. With such arrangement of detectors, the low-energy data is complete, and may be used to reconstruct a high-quality image of low-energy attenuation coefficient, from which structure information may be extracted. The high-energy data is truncated at both ends, resulting in the inner reconstruction problem. The method of the present disclosure may be used to solve the inner reconstruction problem, in order to obtain a reconstruction result of high-energy attenuation coefficient. The photoelectric effect integral and Compton effect integral obtained from decomposition of dual-energy data are also truncated at both ends. The method described in the present disclosure can be used to reconstruct the photoelectric coefficient and Compton coefficient, and further obtain information about atomic number and electron density of material.

In the above several embodiments, part of the high-energy detector units may be replaced with detectors made of different crystal materials, and filter sheets of different materials (such as metals including Cu, Ti, or Ta) may be added between the high- and low-energy detectors. Accordingly, detectors formed of different crystal materials and filtering materials have different spectral responses, and it is possible to obtain data having two or more different system spectra. With such arrangement of detectors, the low-energy data collected in the system is complete, while the two or more types of high-energy data are incomplete. One type of the high-energy data may be selected for use with the low-energy data for reconstruction by the method of the present disclosure. All the data may be used simultaneously for reconstruction of attenuation coefficients at three or more energy levels.

Figure 14:
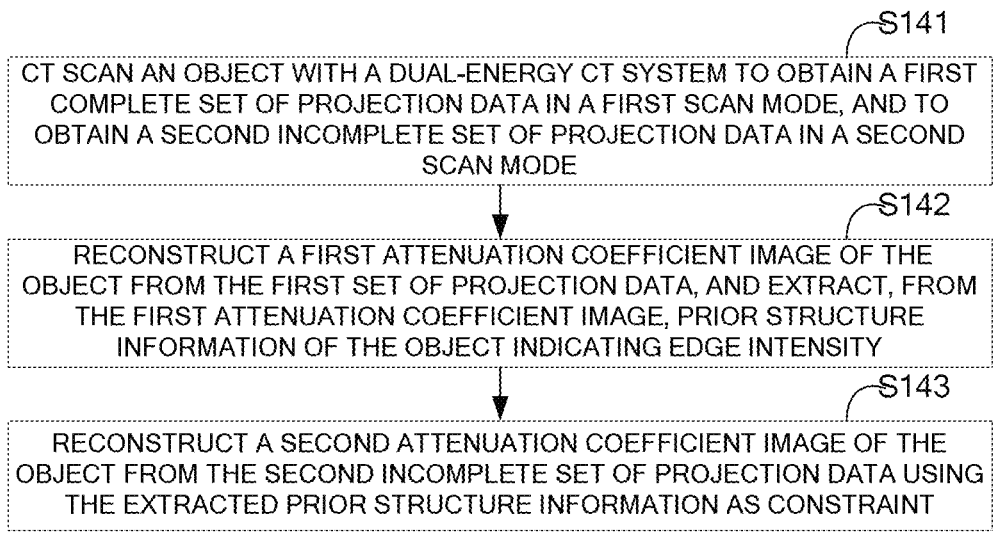
FIG. 14 illustrates a flowchart of a CT imaging method according to an embodiment of the present disclosure.

FIG. 14 illustrates a flowchart of a CT imaging method according to an embodiment of the present disclosure. As shown in FIG. 14, at step S141, an object is CT-scanned by a dual-energy CT system to obtain a first complete set of projection data in a first scan mode, and to obtain a second incomplete set of projection data in a second scan mode.

At step S142, a first attenuation coefficient image of the object is reconstructed from the first set of projection data, and from the first attenuation coefficient image, prior structure information of the object is extracted indicating edge intensity.

At step S143, a second attenuation coefficient image of the object is reconstructed from the second incomplete set of projection data using the extracted prior structure information as a constraint.

In some embodiments, the dual-energy CT system includes multiple rows of low-energy detectors, and high-energy detectors disposed behind part of the rows of low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, a limited-angle CT scan may be performed on the object with rays at a second energy level different from the first energy level, to obtain the second incomplete set of projection data.

In some embodiments, the dual-energy CT system includes multiple low-energy detectors, and multiple high-energy detectors disposed behind the low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, a sparse-angle sampling CT scan may be performed on the object with rays at a second energy level different from the first energy level, to obtain the second incomplete set of projection data.

In some embodiments, the dual-energy CT system may include at least one row of low-energy detectors, and a plurality of high-energy detectors which are uniformly provided behind part of the low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, a detector undersampling CT scan may be performed on the object with rays at a second energy level different from the first energy level, to obtain the second incomplete set of projection data.

In some embodiments, the dual-energy CT system may include at least one row of low-energy detectors, and a plurality of high-energy detectors which are concentrated and provided behind part of the low-energy detectors. A first complete set of projection data may be obtained in a first scan mode. In particular, a 360-degree circular or helical CT scan may be performed on an object with rays at a first energy level, to obtain the first complete set of projection data. A second incomplete set of projection data may be obtained in a second scan mode. In particular, an inner reconstruction CT scan may be performed on the object with rays at a second energy level different from the first energy level, to obtain the second incomplete set of projection data.

In some embodiments, the step of extracting prior structure information of the object from the first attenuation coefficient image may include performing edge extraction on the first attenuation coefficient image to obtain the prior structure information.

Figure 15:
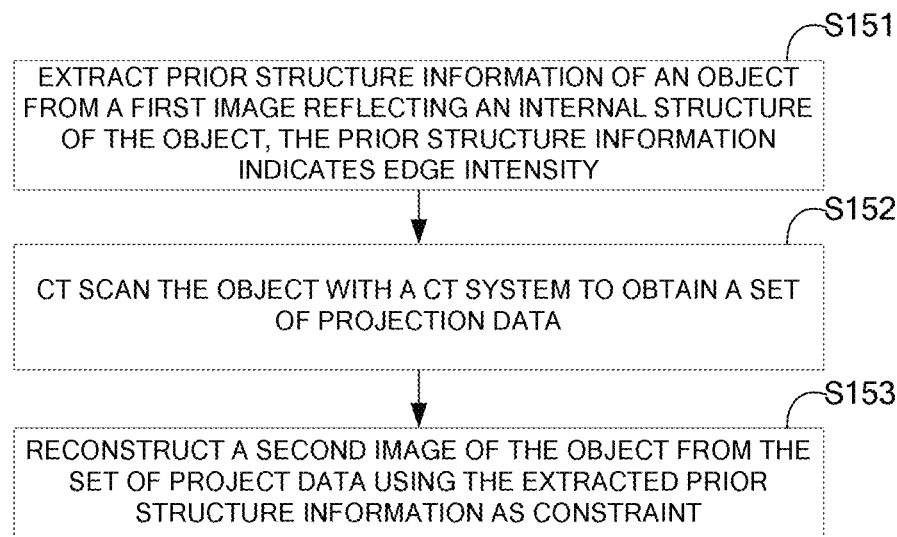
FIG. 15 illustrates as flowchart of a CT imaging method according to another embodiment of the present disclosure.

FIG. 15 illustrates a flowchart of a CT imaging method according to another embodiment of the present disclosure. As shown in FIG. 15, at step S151, prior structure information of an object is extracted from a first image reflecting an internal structure of the object. The prior structure information indicates edge intensity.

At step S152, the object is CT-scanned by a CT system to obtain a set of projection data.

At step S153, a second image of the object is reconstructed from the set of project data using the extracted prior structure information as a constraint.

In some embodiments, the CT system performs a limited-angle CT scan on the object to obtain the set of projection data.

In some embodiments, the CT system performs a sparse-angle sampling CT scan on the object to obtain the set of projection data.

In some embodiments, the CT system performs a detector undersampling CT scan on the object to obtain the set of projection data.

In some embodiments, the CT system performs an inner reconstruction CT scan on the object to obtain the set of projection data.

In some embodiments, the step of extracting prior structure information of the object from the first image may include performing edge extraction on the first image to obtain the prior structure information.

Solutions according to some embodiments are applicable in various fields such as lossless detection, medical diagnosis, and safety inspection. With some embodiments of the present disclosure that using structure information of the reconstructed object as prior information, it is possible to dramatically reduce an amount of projection data required for image reconstruction, without any requirement on the numerical dynamic range of the prior image. The methods of the present disclosure can be used to solve the image reconstruction quality problem due to incomplete data, such as the limited-angle CT scan problem, the sparse-angle sampling CT scan problem, the inner reconstruction CT scan problem, and the detector undersampling CT scan problem, and achieve satisfactory effects. Those skilled in the art will appreciate that embodiments of the present disclosure can be applied in various fields such as medical diagnosis, industrial lossless detection and safety inspection.

Various embodiments of the apparatus and method for producing distributed x-rays have been described in detail with reference to block diagrams, flowcharts, and/or examples. In the case that such block diagrams, flowcharts, and/or examples include one or more functions and/or operations, those skilled in the art will appreciate that each function and/or operation in the block diagrams, flowcharts, and/or examples can be implemented, individually and/or collectively, as various hardware, software, firmware or substantially any combination thereof, in an embodiment, several parts of the subject matters illustrated in the embodiments, such as control process, may be implemented with application specific integrated circuit (ASIC), field programmable gate array (FPGA), digital signal processor (DSP) or any other integrated format. Those skilled in the art will appreciate that some aspects of the embodiments disclosed here, in part or as a whole, may be equivalently implemented in integrated circuit, as one or more computer programs running on one or more computers (e.g., one or more programs running on one or more computer systems), as one or more programs running on one or more processors (e.g., one or more programs running on one or more microprocessors), in firmware, or in substantially any combination thereof. Those skilled in the art are able to design circuits and/or write software and/or firm codes according to the present disclosure. Further, those skilled in the art will appreciate that the control process in the present disclosure can be distributed as various forms of program products. Whatever specific type of signal bearing medium is used to fulfill the distribution, the example embodiments of the subject matters of the present disclosure are applicable. Examples of the signal bearing medium include but not limited to recordable medium, such as floppy disk, hard disk drive, compact disk (CD), digital versatile disk (DVD), digital tape, computer memory, and transmission-type medium, such as digital and/or analog communication medium (e.g., optical fiber cable, waveguide, wired and wireless communication link).

The present invention has been described with reference to several exemplary embodiments. It will be appreciated that the terms used here are for illustration, are exemplary other than limiting. The present invention can be practiced in various forms within the spirit or subject matter of the present invention. It will be appreciated that the foregoing embodiments are not limited to any of the above detailed description, and should be construed in a broad sense within the spirit and scope defined by the appended claims. All changes and variations falling into the scope of the claims or their equivalents should be encompassed by the appended claims.

The invention claimed is:

1. A CT imaging method, comprising:
   CT scanning an object with a dual-energy CT system to obtain a first complete set of projection data at a first energy level, and to obtain a second incomplete set of projection data at a second energy level different from the first energy level;
   reconstructing a first image of the object from the first set of projection data, and extracting, from the first image, prior structure information of the object indicating edge intensity, wherein the extracted prior structure information describes boundaries and details having obvious difference in the first image; and reconstructing a second image of the object from the second incomplete set of projection data using the extracted prior structure information as a constraint.

2. The method according to claim 1, wherein
the dual-energy CT system comprises multiple rows of low-energy detectors, and high-energy detectors disposed behind part of the rows of low-energy detectors;
said obtaining a first complete set of projection data in a first scan mode comprises performing a 360-degree circular or helical CT scan on the object with rays at a first energy level, to obtain the first complete set of projection data;
said obtaining a second incomplete set of projection data in a second scan mode comprises performing a limited-angle CT scan on the object with rays at a second energy level different from the first energy level, to obtain the second incomplete set of projection data.

3. The method according to claim 1, wherein
the dual-energy CT system comprises multiple low-energy detectors, and multiple high-energy detectors disposed behind the low-energy detectors;
said obtaining a first complete set of projection data in a first scan mode comprises performing a 360-degree circular or helical CT scan on the object with rays at a first energy level, to obtain the first complete set of projection data;
said obtaining a second incomplete set of projection data in a second scan mode comprises performing a sparse-angle sampling CT scan on the object with rays at a second energy level different from the first energy level, to obtain the second incomplete set of projection data.

4. The method according to claim 1, wherein
the dual-energy CT system comprises at least one row of low-energy detectors, and a plurality of high-energy detectors which are uniformly provided behind part of the low-energy detectors;
said obtaining a first complete set of projection data in a first scan mode comprises performing a 360-degree circular or helical CT scan on the object with rays at a first energy level, to obtain the first complete set of projection data;
said obtaining a second incomplete set of projection data in a second scan mode comprises performing a detector undersampling CT scan on the object with rays at a second energy level different from the first energy level, to obtain the second incomplete set of projection data.

5. The method according to claim 1, wherein
the dual-energy CT system comprises at least one row of low-energy detectors, and a plurality of high-energy detectors which are concentrated and provided behind part of the low-energy detectors;
said obtaining a first complete set of projection data in a first scan mode comprises performing a 360-degree circular or helical CT scan on the object with rays at a first energy level, to obtain the first complete set of projection data;
said obtaining a second incomplete set of projection data in a second scan mode comprises performing an inner reconstruction CT scan on the object with rays at a second energy level different from the first energy level, to obtain the second incomplete set of projection data.

6. The method according to claim 1, wherein said extracting prior structure information of the object from the first image comprises performing edge extraction on the first image to obtain the prior structure information.

7. The method according to claim 6, wherein said reconstructing a second image of the object from the second incomplete set of projection data comprises:
calculating the second image f according to an equation $$\min\|G\nabla f\|_1 + \lambda\|\nabla f\|_1 = \min\|(G+\lambda I)\nabla f\|_1$$
$$\text{s.t.} \quad \|Hf-p\|_W \le \varepsilon$$

wherein $\varepsilon$ is a quantity related to an overall noise level in the second set of projection data, and $\lambda$ is used to balance a prior structure information constraint and a Total Variation (TV) constraint; the prior structure information constraint is dominant when $\lambda \le 1$, while minimization of the TV is a dominant constraint when $\lambda > 1$; the second image is denoted as $f=\{f_1, f_2, \ldots, f_n\}$, the second set of projection data obtained by the CT scan is denoted as $p=\{p_1, p_2, \ldots, p_m\}$, a line integral projection process is denoted as $$H\{h_{i,j}\}_{m\times n},$$

the prior structure information is denoted as $g=\{g_1, g_2, \ldots, g_n\}$, W is a weighted matrix reflecting noise characteristic of projection data, I is identity matrix, and a weighted matrix is generated from the prior structure information as $G=\text{diag}(g)=\text{diag}\{g_1, g_2, \ldots, g_n\}$; a larger $g_i$ represents a weaker edge, while a smaller $g_i$ represents a stronger edge.

8. The method according to claim 6, wherein said edge extraction is performed using one of Laplace operator, Candy operator, discrete gradient transform, or adaptive thresholding.

9. A CT imaging method, comprising:
extracting prior structure information of an object from a first image reflecting an internal structure of the object, wherein the first image is a design drawing of the object, the prior structure information indicates edge intensity, and the extracted prior structure information describes boundaries and details having obvious difference in the first image;
CT scanning the object with a CT system to obtain a set of projection data; and
reconstructing a second image of the object from the set of projection data using the extracted prior structure information as a constraint.

10. The method according to claim 9, wherein the CT system performs a limited-angle CT scan on the object to obtain the set of projection data.

11. The method according to claim 9, wherein the CT system performs a sparse-angle sampling CT scan on the object to obtain the set of projection data.

12. The method according to claim 9, wherein the CT system performs a detector undersampling CT scan on the object to obtain the set of projection data.

13. The method according to claim 9, wherein the CT system performs an inner reconstruction CT scan on the object to obtain the set of projection data.

14. The method according to claim 9, wherein said extracting prior structure information of the object from the first image comprises performing edge extraction on the first image to obtain the prior structure information.

15. The method according to claim 14, wherein said reconstructing a second image of the object from the set of projection data comprises:
calculating the second image f according to an equation $$\min\|G\nabla f\|_1 + \lambda\|\nabla f\|_1 = \min\|(G+\lambda I)\nabla f\|_1$$
$$\text{s.t.} \quad \|Hf - p\|_W \le \varepsilon$$

wherein $\varepsilon$ is a quantity related to an overall noise level in the second set of projection data, and $\lambda$ is used to balance a prior structure information constraint and a Total Variation (TV) constraint; the prior structure information constraint is dominant when $\lambda \le 1$, while minimization of the TV is a dominant constraint when $\lambda > 1$; the second image is denoted as $f=\{f_1, f_2, \ldots, f_n\}$, the second set of projection data obtained by the CT scan is denoted as $p=\{p_1, p_2, \ldots, p_m\}$, a line integral projection process is denoted as $$H\{h_{ij}\}_{m \times n},$$

the prior structure information is denoted as $g=\{g_1, g_2, \ldots, g_n\}$, W is a weighted martrix reflecting noise characteristic of projection data, I is identity matrix, and a weighted matrix is generated from the prior structure information as $G=\text{diag}(g)=\text{diag}\{g_1, g_2, \ldots, g_n\}$; a larger $g_i$ represents a weaker edge, while a smaller $g_i$ represents a stronger edge.

16. The method according to claim 14, wherein said edge extraction is performed using one of Laplace operator, Candy operator, discrete gradient transform, or adaptive thresholding.

17. The method according to claim 9, wherein the first image is an image reconstructed from a previous CT scan of the object, or a design drawing of the object.

18. A CT imaging system, comprising:
a ray source configured to generate dual-energy X rays;
a detection & collection device configured to receive dual-energy X rays penetrating an object;
a control device configured to control the ray source and the detection & collection device to CT scan the object to obtain a first complete set of projection data at a first energy level, and to obtain a second incomplete set of projection data at a second energy level different from the first energy level; and
a reconstruction device configured to reconstruct a first image of the object from the first set of projection data, extract, from the first image, prior structure information of the object indicating edge intensity, and reconstruct a second image of the object from the second incomplete set of projection data using the extracted prior structure information as a constraint, wherein the extracted prior structure information describes boundaries and details having obvious difference in the first image.

19. A CT imaging system, comprising:
a ray source configured to generate dual-energy X rays;
a detection & collection device configured to receive dual-energy X rays penetrating an object; a control device configured to control the ray source and the detection & collection device to CT scan the object to obtain a set of projection data; and
a reconstruction device configured to extract prior structure information of the object from a first image reflecting an internal structure of the object, wherein the first image is a design drawing of the object, the prior structure information indicates edge intensity, and reconstruct a second image of the object from the set of projection data using the extracted prior structure information as a constraint, wherein the extracted prior structure information describes boundaries and details having obvious difference in the first image.

20. The system according to claim 19, wherein the first image is an image reconstructed from a previous CT scan of the object, or a design drawing of the object.

* * * * *